United States Patent [19]

Hesse

[11] Patent Number: Plant 6,552

[45] Date of Patent: Jan. 24, 1989

[54] CHRYSANTHEMUM PLANT NAMED MAJESTIC

[75] Inventor: Peter S. Hesse, Bradenton, Fla.

[73] Assignee: Ball Pan Am Plant Co., Parrish, Fla.

[21] Appl. No.: 56,983

[22] Filed: Jun. 3, 1987

[51] Int. Cl.[4] ..... A01H 5/00

[52] U.S. Cl. ..... Plt./76

[58] Field of Search ..... Plt./74–82

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Majestic, characterized by its medium to dark lavender flower color; vigorous growth habit; double flower form; dense and relatively large diameter capitulum; 9 week response period.

1 Drawing Sheet

The present invention comprises a new and distinct cultivar of *Chrysanthemum morifolium,* Ramat., hereinafter referred to by the cultivar name Majestic.

Majestic is a product of a planned breeding program which had the objective of creating new Chrysanthemum cultivars having large dark lavender decorative flowers on a plant exhibiting excellent habit when grown year round, and producing numerous breaks when the plants are pinched. Such traits in combination were not present in previously available commercial cultivars.

Majestic was originated from a hybridization made by Peter S. Hesse in a controlled breeding program in West Chicago, Ill. in 1980. The female parent was the cultivar Distinctive. The male parent of Majestic was the cultivar Burgundy. Majestic was discovered and selected as one flowering plant within the progeny of the stated parentage by applicant in November 1981 in a controlled environment in Bradenton, Fla.

The first act of asexual reproduction of Majestic was accomplished when vegetative cuttings were taken from the initial selection in March 1982 in a controlled environment in Parrish, Fla. by a technician working under formulations established and supervised by applicant. Horticultural examination of selected units initiated in May 1982 has demonstrated that the combination of characteristics as herein disclosed for Majestic are firmly fixed and are retained through successive generations of asexual reproduction.

The following traits have been repeatedly observed and are determined to be basic characteristics of Majestic, which in combination distinguish this Chrysanthemum as a new and distinct cultivar:

1. Nine week response period.
2. Vigorous growth habit.
3. A very double flower form with few disc florets present.
4. Diameter of capitulum 10–12 cm.
5. Individual florets range up to 60 mm long at outer edge of capitulum (fully expanded petals).
6. A very dense flower, with approximately 510 ray florets per capitulum.
7. Finished height 20–25 cm above the edge of the pot depending upon growing conditions and growth regulator applications.
8. Flower color is dark lavender under winter growing conditions and medium lavender with no color breaking under summer growing conditions.

Majestic has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

Of the many commercial cultivars known to the present inventor, the most similar in comparison to Majestic is Deep Hotpink. In comparison to Deep Hotpink, Majestic has wider ray florets, the entire flower is more reflexed and exhibits less color fading as flowers mature.

The accompanying photographic drawing shows typical inflorescence and foliage characteristics of Majestic. The photograph is in black and white, with three flowers being colored to accurately depict true flower color.

In the following description, color references are made to The Royal Horticultural Society Color Chart. The color values were determined between 9 and 10 a.m. on Apr. 22, 1987 under fluorescent light at Parrish, Fla.

Classification:

*Botanical.*—*Chrysanthemum morifolium,* Ramat., cv. Majestic.

*Commercial.*—Decorative pot.

INFLORESCENCE

A. Capitulum:

*Form.*—Flat.

*Type.*—Double.

*Diameter across face.*—10–12 cm.

B. Corolla of ray florets:

*Color (general tonality from a distance of three meters).*—Medium lavender.

*Color (upper surface).*—78B.

*Color (under surface).*—78D.

C. Corolla of disc florets:

*Color (mature).*—Yellow.

*Color (immature).*—Lime green.

D. Reproductive organs:

*Androecium.*—Very few; present in disc florets only.

*Gynoecium.*—Present in both disc and ray florets.

PLANT

A. General appearance:

*Height.*—20–24 cm above the edge of the pot.

B. Foliage:

*Color* (*upper surface*).—147A.

*Color* (*under surface*).—147B.

*Shape.*—Ovate, deeply lobed with crenate leaf margins.

I claim:

1. A new and distinct cultivar of Chrysanthemum plant named Majestic, as illustrated and described, and particularly characterized by its medium to dark lavender flower color; vigorous growth habit; double flower form; dense and relatively large diameter capitulum, and its 9 week response period.

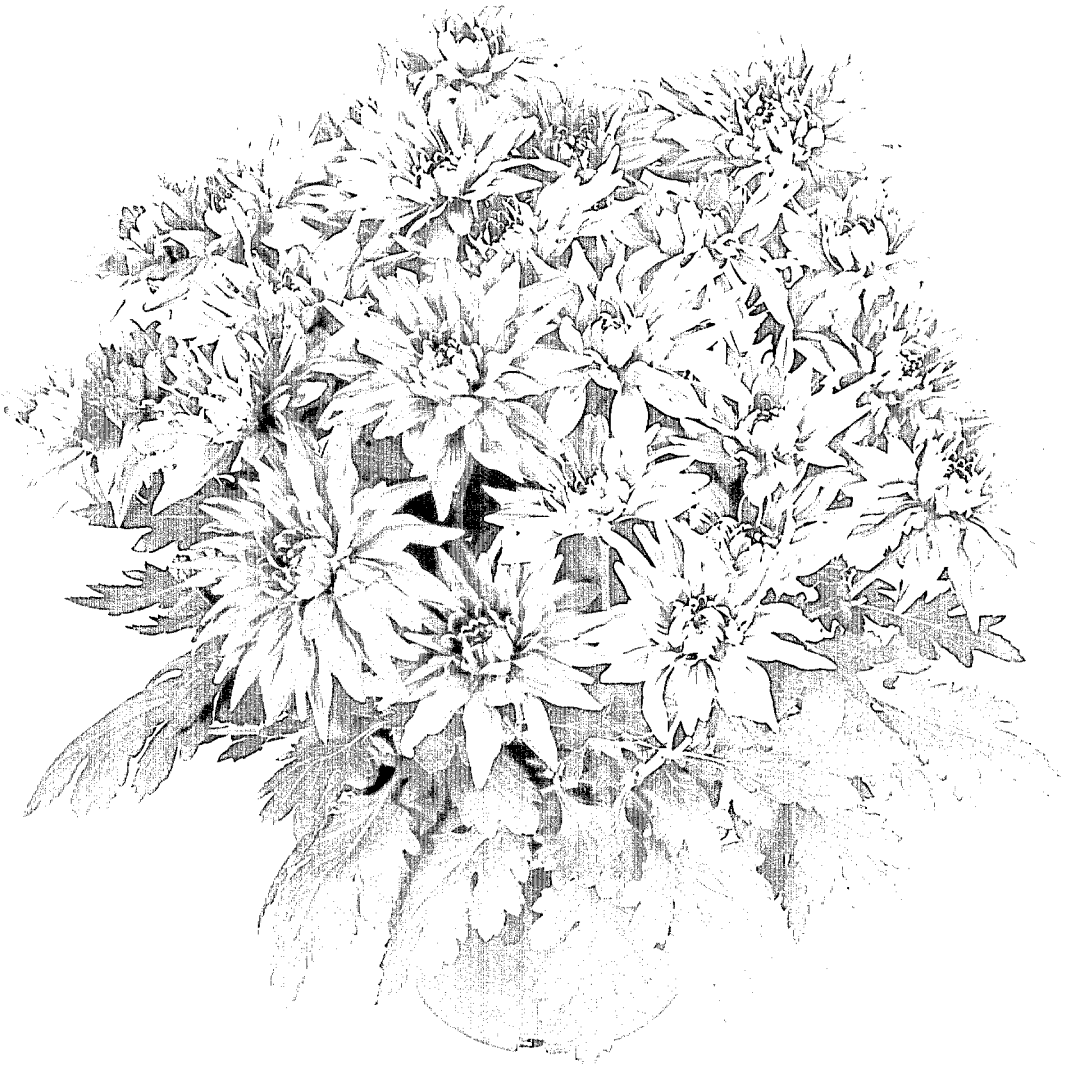

* * * * *